(12) United States Patent
Fei et al.

(10) Patent No.: US 10,576,014 B2
(45) Date of Patent: Mar. 3, 2020

(54) THERAPEUTIC HEAT ENERGY MEASURING SYSTEM, METHOD AND APPLICATION FOR MERIDIAN THERMAL THERAPY DEVICE

(71) Applicant: Shanghai DARONG-MED Ltd., Shanghai (CN)

(72) Inventors: Jianbin Fei, Shanghai (CN); Yan Huang, Shanghai (CN)

(73) Assignee: Shanghai DARONG-MED Ltd., Shanghai (CN)

( * ) Notice: Subject to any disclaimer, the term of this patent is extended or adjusted under 35 U.S.C. 154(b) by 0 days.

(21) Appl. No.: 16/309,421

(22) PCT Filed: Jun. 27, 2017

(86) PCT No.: PCT/CN2017/090239
§ 371 (c)(1),
(2) Date: Dec. 12, 2018

(87) PCT Pub. No.: WO2017/215674
PCT Pub. Date: Dec. 21, 2017

(65) Prior Publication Data
US 2019/0192381 A1  Jun. 27, 2019

(30) Foreign Application Priority Data
Jun. 14, 2016  (CN) .......................... 2016 1 0415901

(51) Int. Cl.
*A61H 39/06*  (2006.01)
*A61F 7/00*  (2006.01)
*G16H 20/30*  (2018.01)

(52) U.S. Cl.
CPC .............. *A61H 39/06* (2013.01); *A61F 7/00* (2013.01); *G16H 20/30* (2018.01);
(Continued)

(58) Field of Classification Search
CPC ...... A61F 2007/0071; A61F 2007/0093; A61F 2007/0096; A61F 7/00; A61H 2201/5007; A61H 39/06; G16H 20/30
(Continued)

(56) References Cited

U.S. PATENT DOCUMENTS

| 2004/0044384 | A1* | 3/2004 | Leber ................... | A61N 5/0619 607/88 |
| 2012/0289873 | A1* | 11/2012 | Ma ........................ | A61H 9/0078 601/18 |
| 2017/0087005 | A1* | 3/2017 | Na ........................ | A61H 39/06 |

FOREIGN PATENT DOCUMENTS

| CN | 201516145 U | 6/2010 |
| CN | 103126881 A | 6/2013 |

(Continued)

OTHER PUBLICATIONS

International Search Report and Written Opinion dated Sep. 20, 2017, for corresponding International Application No. PCT/CN2017/090239; International Filing Date: Jun. 27, 2017 consisting of 5-pages. (Year: 2017).*

*Primary Examiner* — Kaitlyn E Smith
*Assistant Examiner* — Christine A Dedoulis
(74) *Attorney, Agent, or Firm* — IPro, PLLC; Na Xu (57) ABSTRACT

A therapeutic thermal energy measuring system, method and application for a meridian thermal therapy device. The therapeutic thermal energy measuring system for a meridian thermal therapy device comprises: a time setting module for setting a time; a temperature setting module or an intensity level setting module for setting a temperature or an intensity level; a therapeutic thermal energy measuring module for measuring therapeutic thermal energy on the basis of a preset time and a preset temperature or intensity level, and outputting a result, and/or performing real-time measurement of therapeutic thermal energy on the basis of a preset
(Continued)

temperature or intensity level and cumulative working hours of a treatment head of the meridian thermal therapy device, and outputting a result. The therapeutic heat energy measuring system can solve a bottleneck problem of having no way of quantizing therapeutic thermal energy in meridian thermal therapy.

6 Claims, 3 Drawing Sheets (52) U.S. Cl.
CPC ............ *A61F 2007/0071* (2013.01); *A61F 2007/0093* (2013.01); *A61F 2007/0096* (2013.01); *A61H 2201/0173* (2013.01); *A61H 2201/0221* (2013.01); *A61H 2201/1207* (2013.01); *A61H 2201/50* (2013.01); *A61H 2201/5007* (2013.01); *A61H 2201/5023* (2013.01); *A61H 2205/00* (2013.01)

(58) Field of Classification Search
USPC ........................................... 607/108
See application file for complete search history.

(56) References Cited

FOREIGN PATENT DOCUMENTS

| | | |
|---|---|---|
| CN | 105616149 A | 6/2016 |
| CN | 205286914 U | 6/2016 |
| CN | 106038262 A | 10/2016 |
| CN | 205924473 U | 2/2017 |
| KR | 20150136281 A | 12/2015 |

* cited by examiner

THERAPEUTIC HEAT ENERGY MEASURING SYSTEM, METHOD AND APPLICATION FOR MERIDIAN THERMAL THERAPY DEVICE

TECHNICAL FIELD

The invention relates to the field of medical instruments, in particular relates to a therapeutic heat energy measuring system, method and application of a meridian thermal therapy device.

BACKGROUND

Moxibustion is one of the three core inventions of Chinese medicine (Chinese herbal medicine, acupuncture, moxibustion). The original moxibustion method burns on the acupoints by burning Ai, which is used to treat diseases and prevent diseases, and has a simple method and remarkable curative effect. However, due to the "smog" in the process of burning, the treatment needs to be carried out in a relatively closed treatment institution or living room, so it is difficult to be widely accepted, especially in developed countries. In recent decades, there have been many electronic moxibustion treatment devices that use electronic temperature-controlled heating technology instead of burning Al fever. Although the troubles of smog have been avoided, there are still problems:

1. The essence of traditional moxibustion is a natural treatment for injecting "appropriate heat energy" into acupuncture points in the human body under suitable temperature conditions. So far, there have been non-uniform variables such as the number of column Ai, "strong" (cone moxa), "Make a few minutes of moxibustion", "Make a few minutes of bird pecking moxibustion", "Make a few minutes of moxibustion moxa swirling", but due to the uncontrollable factors such as the thickness of the moxa, the ratio of the moxa, the distance between the burning and the acupoints, there is no uniform standard.

2. When using meridian thermal therapy in different human bodies, different acupoints, different diseases and different solar terms, the setting of temperature, time and heat directly affects the efficacy of meridian thermal therapy and the side effects. Therefore, the lack of professional standards will directly restrict the wide application of meridian thermal therapy.

3. Although the electronic temperature control heating technology has controllable temperature and time, there is no standardization measurement, display, storage and transmission mode for the input of meridian treatment heat, which has made it impossible to compile standardized moxibustion "acupoint prescription".

SUMMARY

The invention is intended to provide a therapeutic heat energy measuring system, method and application of a meridian thermal therapy device. The therapeutic heat energy measuring system of the invention comprising: a time setting module for setting time; a temperature setting module or an intensity level module for setting temperature or intensity level; a therapeutic thermal energy measurement module for measuring therapeutic thermal energy on the basis of a preset time and a preset temperature or intensity level by formula 1a, and outputting a result, and/or performing real-time measurement of therapeutic thermal energy on the basis of a preset temperature or intensity level and cumulative working hours of a treatment head of the meridian thermal therapy device by formula 1b, and outputting a result. The invention have a special, simple and convenient therapeutic heat energy measuring system for a meridian thermal therapy device, realizes the measurement of meridian thermal therapy with radiation therapeutically thermal energy, and makes the operation and control more convenient and accurate.

In order to achieve the above and other related purposes, the present invention provides a therapeutic heat energy measuring system, method and application of a meridian thermal therapy device.

The first aspect of the invention provides a therapeutic heat energy measuring system of a meridian thermal therapy device, comprising: a time setting module for setting time; a temperature setting module or an intensity level setting module for setting temperature or intensity level; a therapeutic thermal energy measurement module for measuring therapeutic thermal energy on the basis of a preset time and a preset temperature or intensity level by formula 1a, and outputting a result, and/or performing real-time measurement of therapeutic thermal energy on the basis of a preset temperature or intensity level and cumulative working hours of a treatment head of the meridian thermal therapy device by formula 1b, and outputting a result;

$$Q = I^2 R t_s [p_r + (T_s - T_0) \times \gamma]; \quad \text{formula 1a:}$$

$$Q_w = I^2 R t_w [p_r + (T_s - T_0) \times \gamma]; \quad \text{formula 1b:}$$

wherein, Q is a therapeutic thermal energy value; $Q_w$ is a therapeutic thermal energy value cumulatively generated by the treatment head of the meridian thermal therapy device; I is a current value of the meridian thermal therapy device; R is a resistance value of the meridian thermal therapy device; $T_s$ is a preset time; $t_w$ is a cumulative working time of the treatment head of the meridian thermal therapy device; $p_r$ is an initial on-off ratio of the meridian thermal therapy device; $T_s$ is a preset temperature or a temperature according to the preset intensity level; $T_0$ is a punctuation temperature of the meridian thermal therapy device or a temperature according to a punctuation intensity level; γ is an on-off ratio change coefficient.

Preferably, the therapeutic thermal energy measurement module further calculating the therapeutic thermal energy by using formula 2a or 2b:

$$F = \frac{Q}{\delta}; \quad \text{formula 2a}$$

$$F = \frac{Q}{\delta}; \quad \text{formula 2b}$$

wherein, F is a therapeutic thermal energy count value; $F_w$ is a therapeutic thermal energy count value cumulatively generated by the treatment head of the meridian thermal therapy device; δ is a conversion therapeutic thermal energy coefficient of the therapeutic thermal energy count value.

More preferably, the value of δ is (75-125) Cal/FU or (75-125) Cal/Kettle when the unit of measurement of the therapeutic thermal energy count value is FU or Kettle and the unit of measurement of the therapeutic thermal energy is transformed to Cal.

Further, the therapeutic heat energy measuring system comprising:

a therapeutic thermal energy setting module for setting therapeutic thermal energy;

a thermal therapy time measurement module for performing calculation of the required measuring thermal energy according to the preset therapeutic thermal energy and preset temperature or intensity level using formula 3 or 4, and outputting results;

$$t = \frac{Q_s}{I^2 R[p_t + (T_s - T_0) \times \gamma]};\quad \text{formula 3}$$

$$t = \frac{F_s \delta}{I^2 R[p_t + (T_s - T_0) \times \gamma]};\quad \text{formula 4}$$

wherein, t is a working time of the treatment head; $Q_s$ is a preset therapeutic thermal energy value; $F_s$ is a preset therapeutic thermal energy count value; $\delta$ is a conversion thermal energy coefficient of the therapeutic thermal energy count value; I is a current value of the meridian thermal therapy device; R is a resistance value of the meridian thermal therapy device; $p_t$ is an initial on-off ratio of the meridian thermal therapy device; $T_s$ is a preset temperature or a temperature according to the preset intensity level; $T_0$ is a punctuation temperature of the meridian thermal therapy device or a temperature according to a punctuation intensity level; $\gamma$ is an on-off ratio change coefficient.

The second aspect of the invention provides a therapeutic thermal energy measurement method of a meridian thermal therapy device, wherein comprising following steps:

Step S101, setting time;

Step S102, setting temperature or intensity level;

Step S103, measuring therapeutic thermal energy on the basis of a preset time and a preset temperature or intensity level by formula 1a, and outputting a result, and/or performing real-time measurement of therapeutic thermal energy on the basis of a preset temperature or intensity level and cumulative working hours of a treatment head of the meridian thermal therapy device by formula 1b, and outputting a result;

$$Q = I^2 R t_s [p_t + (T_s - T_0) \times \gamma];\quad \text{formula 1a:}$$

$$Q_w = I^2 R t_w [p_t + (T_s - T_0) \times \gamma];\quad \text{formula 1b:}$$

wherein, Q is a therapeutic thermal energy value; $Q_w$ is a therapeutic thermal energy value cumulatively generated by the treatment head of the meridian thermal therapy device; I is a current value of the meridian thermal therapy device; R is a resistance value of the meridian thermal therapy device; $T_s$ is a preset time; $t_w$ is a cumulative working time of the treatment head of the meridian thermal therapy device; $p_t$ is an initial on-off ratio of the meridian thermal therapy device; $T_s$ is a preset temperature or a temperature according to the preset intensity level; $T_0$ is a punctuation temperature of the meridian thermal therapy device or a temperature according to a punctuation intensity level; $\gamma$ is an on-off ratio change coefficient.

Preferably, counting the therapeutic thermal energy by using formula 2a or 2b in Step 103:

$$F = \frac{Q}{\delta};\quad \text{formula 2a}$$

$$F = \frac{Q}{\delta};\quad \text{formula 2b}$$

wherein, F is a therapeutic thermal energy count value; $F_w$ is a therapeutic thermal energy count value cumulatively generated by the treatment head of the meridian thermal therapy device; $\delta$ is a conversion therapeutic thermal energy coefficient of the therapeutic thermal energy count value.

More preferably, the value of $\delta$ is (75-125) Cal/FU or (75-125) Cal/Kettle when the unit of measurement of the therapeutic thermal energy count value is FU or Kettle and the unit of measurement of the therapeutic thermal energy is transformed to Cal.

Further, the therapeutic thermal energy measurement method further comprising a following step:

Step 104, setting therapeutic thermal energy;

Step 105, performing calculation of the required measuring thermal energy according to the preset therapeutic thermal energy and preset temperature or intensity level using formula 3 or 4, and outputting results;

$$t = \frac{Q_s}{I^2 R[p_t + (T_s - T_0) \times \gamma]};\quad \text{formula 3}$$

$$t = \frac{F_s \delta}{I^2 R[p_t + (T_s - T_0) \times \gamma]};\quad \text{formula 4}$$

wherein, t is a working time of the treatment head; $Q_s$ is a preset therapeutic thermal energy value; $F_s$ is a preset therapeutic thermal energy count value; $\delta$ is a conversion thermal energy coefficient of the therapeutic thermal energy count value; I is a current value of the meridian thermal therapy device; R is a resistance value of the meridian thermal therapy device; $p_t$ is an initial on-off ratio of the meridian thermal therapy device; $T_s$ is a preset temperature or a temperature according to the preset intensity level; $T_0$ is a punctuation temperature of the meridian thermal therapy device or a temperature according to a punctuation intensity level; $\gamma$ is an on-off ratio change coefficient.

The third aspect of the invention provides a meridian thermal therapy device, the meridian thermal therapy device comprising a therapeutic heat energy measuring system which is the therapeutic heat energy measuring system in any one of the above items.

As mentioned above, the therapeutic heat energy measuring system, method and application of the meridian thermal therapy device of the present invention has at least one of the following beneficial effects:

1) The invention is based on the characteristics that the treatment head of the meridian thermal therapy directly adheres to the skin and is less affected by environmental factors, and the thermal energy generated by the meridian thermotherapy instrument is used as a parameter for measuring the thermal energy, and the therapeutic thermal energy in the meridian thermal therapy is solved. It is impossible to unify the problem of quantitative specification, and has a special, simple and convenient therapeutic thermal energy metering system and measurement method for meridian thermal therapy, which realizes the measurement of thermal energy by the thermal energy emitted by the treatment head, and provides a strong scientific basis for the standardization of meridian thermal therapy.

2) The doctor can according to the therapeutic thermal energy metering system and method of the meridian thermotherapy device of the present invention, and the "acupoint prescription" of the meridian thermal therapy required by the patient, changes the pattern of traditional Chinese medicine moxibustion, and greatly improves the meridian thermal therapy. Reliability and standardization of actual operation and efficacy evaluation;

3) By using the formula 2a or 2b for the treatment of thermal energy, it can be solved that the "Joule" unit is too small to cause the count to be too large. If the reading is a few hundred thousand "Joule" as the unit of measurement, the "Acupoint prescription" is issued. It is obviously not convenient enough when recording;

4) According to the present invention, the therapeutic thermal energy count value is FU (Chinese "kettle"), which is intended to be the Fei's Unit of the inventor's last name of Zao Cheng Fei, and the Chinese "kettle" is the volume name of the Spring and Autumn Warring States period, and may also be a capacity unit. It can guide people to use the concept of capacity to "kettle" the therapeutic thermal energy obtained by meridian thermal therapy, easy to remember, to avoid the excess and deficiency of meridian thermal therapy.

DETAILED DESCRIPTION

The embodiments of the present invention are described below by way of specific examples, and those skilled in the art can understand other advantages and effects of the present invention from the disclosure of the present disclosure. The present invention may be embodied or applied in various other specific embodiments, and various modifications and changes may be made without departing from the spirit and scope of the invention.

Please refer to FIG. 1 to FIG. 4. It should be noted that the illustrations provided in the present embodiment merely illustrate the basic concept of the present invention in a schematic manner, so that only the components and layouts related to the present invention are shown in the drawings, instead of the number of components in actual implementation, The shape and size are drawn, and the number of components in actual implementation can be a random change, and the component layout type can be more complicated.

Embodiment 1

Figure 1:
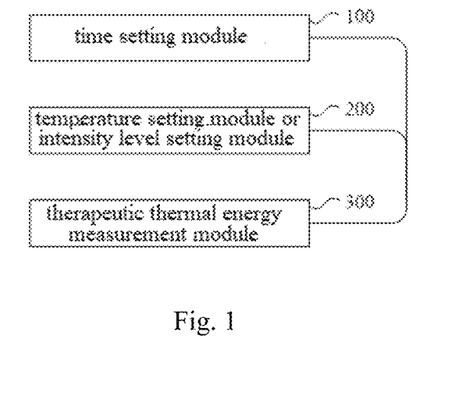
FIG. 1 shows a therapeutic thermal measuring system of a meridian thermal therapy device according to embodiment 1 of the present invention.

FIG. 1 shows a therapeutic heat energy measuring system of a meridian thermal therapy device, comprising:

a time setting module 100 for setting time;

a temperature setting module or an intensity level setting module 200 for setting temperature or intensity level;

a therapeutic thermal energy measurement module 300 for measuring therapeutic thermal energy on the basis of a preset time and a preset temperature or intensity level by formula 1a, and outputting a result, and/or performing real-time measurement of therapeutic thermal energy on the basis of a preset temperature or intensity level and cumulative working hours of a treatment head of the meridian thermal therapy device by formula 1b, and outputting a result;

$$Q=I^2Rt_s[p_t+(T_s-T_0)\times\gamma];\qquad\text{formula 1a:}$$

$$Q_w=I^2Rt_w[p_t+(T_s-T_0)\times\gamma];\qquad\text{formula 1b:}$$

wherein, $Q$ is a therapeutic thermal energy value; $Q_w$ is a therapeutic thermal energy value cumulatively generated by the treatment head of the meridian thermal therapy device; $I$ is a current value of the meridian thermal therapy device; $R$ is a resistance value of the meridian thermal therapy device; $T_s$ is a preset time; $t_w$ is a cumulative working time of the treatment head of the meridian thermal therapy device; $p_t$ is an initial on-off ratio of the meridian thermal therapy device; $T_s$ is a preset temperature or a temperature according to the preset intensity level; $T_0$ is a punctuation temperature of the meridian thermal therapy device or a temperature according to a punctuation intensity level; $\gamma$ is an on-off ratio change coefficient.

$Q$ is a preset therapeutic thermal energy generated by the treatment head of the meridian thermal therapy device, in the unit of Jouler;

$Q_w$ is a therapeutic thermal energy cumulatively generated by the treatment head of the meridian thermal therapy device, in the unit of Joule;

$I$ is a current intensity of the meridian thermal therapy device when the meridian thermal therapy device is electrified, in the unit of Ampere; generally, the current intensity of the meridian thermal therapy device is a fixed value.

$R$ is a resistance value of the meridian thermal therapy device, in the unit of Ohm; generally, the resistance value of the meridian thermal therapy device is also a fixed value.

$T_s$ is a preset time of the working time of the treatment head of the meridian thermal therapy device, in the unit of Second;

$t_w$ is a cumulative working time of the treatment head of the meridian thermal therapy device, in the unit of Second;

$p_t$ is an initial on-off ratio of the meridian thermal therapy device, the on-off ratio refers to the ratio of the total on-off time to the total on-off time and off-off time of the heating element of the treatment head of the meridian thermal therapy device under the working status, that is $t_{on}/(t_{on}+t_{off})$. The initial switching-off ratio refers to the ratio of the initial switching-on time to the sum of the switching-off time and the total switching-off time of the heating element of the treatment head of the meridian thermal therapy device under the working status. In order to prevent the temperature of the treatment head from rising continuously, even in the working state, the heating element of the treatment head of the meridian thermal therapy device is not always electrified, it's the alternating interval between power on and power off. The initial on-off ratio refers to the preset on-off ratio of the treatment head of the meridian thermal therapy device. The initial on-off ratio has been preset in the device production process. The actual on-off ratio can be increased or decreased compared with the initial one by adjusting the temperature or level (such as changing the power-off time or changing the power-on time).

$T_s$ is a preset temperature of the treatment head of the meridian thermal therapy device or a preset temperature of the treatment head of the meridian thermal therapy device according to preset intensity level;

$T_0$ is a punctuation temperature of the meridian thermal therapy device or a temperature according to a punctuation intensity level; $\gamma$ is an on-off ratio change coefficient without unit.

It will be readily apparent to those skilled in the art that the therapeutic thermal energy metering process as described above can be implemented using prior art computers, integrated circuit modules, programmable logic devices, other hardware, or existing software modules.

The treatment head of meridian thermal therapy device refers to the parts directly contacted with human acupoint skin, which utilizes the heat energy generated by the treatment head to implement the thermal energy input to the corresponding meridians to produce targeted therapeutic effect.

"Joule" is a general basic unit of heat energy value, and thermal therapy usually requires more heat (usually hundreds or thousands of joules). Therefore, the therapeutic thermal energy measurement module further counting the therapeutic thermal energy by using formula 2a or 2b:

$$F = \frac{Q}{\delta};\quad \text{formula 2a}$$

$$F_w = \frac{Q}{\delta};\quad \text{formula 2b}$$

wherein, F is a therapeutic thermal energy count value; $F_w$ is a therapeutic thermal energy count value cumulatively generated by the treatment head of the meridian thermal therapy device; δ is a conversion heat energy coefficient of the therapeutic thermal energy count value. The therapeutic thermal energy count is designed to make the measurement of thermal energy simpler and clearer. The value of δ and its unit can be set according to the requirements of the instrument designer. For example, assuming that the unit of the therapeutic thermal energy count value is FU or Kettle, if the unit of the therapeutic thermal energy count value is Calorie, presupposed 1FU equals any value in 75-125 Cal, that is the value of δ is any in 75-125 Cal, for example δ is 75 Cal/FU, then when the therapeutic thermal energy count value is 75 Cal, the therapeutic thermal energy count value is 1FU. If the unit of the therapeutic thermal energy count value is Joule, convert between thermal unit Joule and Cal or between unit Cal/FU and Joule/FU of δ according to the present technology.

In order to facilitate measurement, the initial on-off ratio of the device and/or the resistance value of the treatment head and/or the current value of the device can be set at the stage of device manufacture, so that treatment head can produce exactly 1FU thermic energy when working under $T_0$ for 30 minutes, and $T_0$ is the most commonly used temperature (e.g. 43° C.).

The meridian thermal therapy device usually comprises a controlling unit for controlling the working time and working temperature of the treatment head, all the time setting module, the temperature module or the intensity level setting module should be connected with the controlling unit.

The user sets the working time of the treatment head of the meridian thermal therapy device through the time setting module and the temperature setting module or the intensity level setting module to set the temperature of the treatment head of the meridian thermal therapy device or the intensity level of the treatment head of the meridian thermal therapy device. The device uses formula 1a to measure therapeutic thermal energy through therapeutic thermal energy measurement module or uses formula 1a or 2a to measure therapeutic thermal energy and output the results, in order to make the user understand the therapeutic thermal energy that can be generated under the setting level and time. Further, the device can also uses formula 1b to measure therapeutic thermal energy through cumulative working time of the treatment head of the meridian thermal therapy device or uses formula 1b or 2b to measure therapeutic thermal energy and output the results, in order to make the user understand the therapeutic thermal energy in real time.

Embodiment 2

Figure 2:
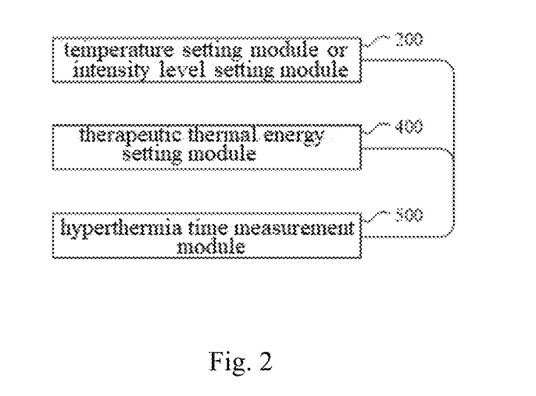
FIG. 2 shows a therapeutic thermal measuring system of a meridian thermal therapy device according to embodiment 2 of the present invention.

FIG. 2 is a therapeutic heat energy measuring system of meridian thermal therapy device according to embodiment 2 of the present invention, on the therapeutic heat energy measuring system of embodiment 1, it further comprising:

a therapeutic thermal energy setting module 400 for setting therapeutic thermal energy; the preset therapeutic thermal energy can be either a preset therapeutic thermal energy or a preset therapeutic thermal energy count value.

A thermal therapy time measurement module 500 for performing calculation of the required measuring thermal energy according to the preset therapeutic thermal energy and preset temperature or intensity level using formula 3 or 4, and outputting results; the thermal therapy time measurement module is usually connected to the controlling unit of the meridian thermal therapy device, and the working time of the treatment head of the meridian thermal therapy device should be controlled according to the output of the thermotherapy time measurement module.

$$t = \frac{Q_s}{I^2 R[p_t + (T_s - T_0) \times \gamma]};\quad \text{formula 3}$$

$$t = \frac{F_s \delta}{I^2 R[p_t + (T_s - T_0) \times \gamma]};\quad \text{formula 4}$$

wherein, t is a working time of the treatment head; $Q_s$ is a preset therapeutic thermal energy value; $F_s$ is a preset therapeutic thermal energy count value; δ is a conversion thermal energy coefficient of the therapeutic thermal energy count value; I is a current value of the meridian thermal therapy device; R is a resistance value of the meridian thermal therapy device; $p_t$ is an initial on-off ratio of the meridian thermal therapy device; $T_s$ is a preset temperature or a temperature according to the preset intensity level; $T_0$ is a punctuation temperature of the meridian thermal therapy device or a temperature according to a punctuation intensity level; γ is an on-off ratio change coefficient.

t is the time required for the therapeutic thermal energy generated by the treatment head of the meridian thermal therapy device is $Q_s$, in the unit of Second;

$Q_s$ is a preset therapeutic thermal energy, in the unit of Joule generated by the treatment head of the meridian thermal therapy device, in the unit of Joule;

$F_s$ is a preset therapeutic thermal energy count value generated by the treatment head of the meridian thermal therapy device; because the therapeutic thermal energy count is simpler and clearer, doctors can directly use the therapeutic thermal energy to prescribe. This is easier to directly prescribe using calorific value. It is more advisable to use a specific integer FU or Kettle value. For example, if the patient need to receive 2FU heat energy at a certain acupoint, the user only needs to input the selected FU value in the corresponding treatment head of the meridian thermal therapy device.

$T_s$ is a preset temperature of the treatment head of the meridian thermal therapy device or preset temperature according to the intensity level of the treatment head of the meridian thermal therapy device, in the unit of ° C.;

It will be readily apparent to those skilled in the art that the therapeutic thermal energy metering process, the thermal therapy time metering process, and the thermal therapy time control as described above may utilize prior art computers, integrated circuit modules, programmable logic devices, other hardware, or existing ones. Software modules are implemented.

According to the therapeutic thermal energy counting value or the therapeutic thermal energy in the acupoint prescription, the user sets the therapeutic thermal energy through the therapeutic thermal energy setting module 400 and sets a comfortable intensity or temperature through temperature setting module or intensity level setting module 200, the device can calculate the corresponding thermal therapy time through the thermal therapy time measurement module 500. Further, thermal therapy time measurement module is connected with the controlling unit of the meridian thermal therapy device. The working time of the treatment head of the meridian thermal therapy device can be controlled according to the outputting results of the thermal therapy time measurement module, so that the therapeutic thermal energy count value (such as FU/Kettle) or the therapeutic thermal energy in the acupoint prescription can be accurately accorded.

Embodiment 3

The therapeutic heat energy measuring system of embodiment 1 or embodiment 2 further comprising:

a data storage module for storing one or more of the preset time, preset temperature or intensity level, a measured therapeutic thermal energy, a measured thermal energy count, a preset therapeutic thermal energy, a preset therapeutic thermal energy count, a measured meridian thermal therapy time, a remaining therapeutic thermal energy, a remaining meridian thermal therapy time.

A remaining therapeutic thermal energy can be a remaining therapeutic thermal energy or a remaining therapeutic thermal energy count value. The remaining therapeutic thermal energy is equal to the preset therapeutic thermal energy or the measured calorific value minus the therapeutic thermal energy value measured by formula 1b. The remaining therapeutic thermal energy count value is equal to the preset therapeutic thermal energy count value or the measured therapeutic thermal energy value minus the therapeutic thermal energy count value measured by formula 1b and formula 2b.

The data storage module is selectively connectable to one or more of the following modules: a time setting module, a temperature setting module or intensity level setting module, a therapeutic thermal measuring module, a therapeutic thermal energy setting module, and a thermal therapy time measurement module and a thermal therapy time control module.

The data storage module should generally be placed in a meridian thermotherapy device, and data can be stored by a storage medium, which can be realized by prior art skilled in the art.

It will be readily apparent to those skilled in the art that the therapeutic thermal energy metering process, the thermal therapy time metering process, and the thermal therapy time control as described above may utilize prior art computers, integrated circuit modules, programmable logic devices, other hardware, or existing ones. Software modules are implemented.

Embodiment 4

The therapeutic thermal energy measuring system of Embodiment 1, Embodiment 2 or Embodiment 3 further comprising:

a display module for displaying one or more of the preset time, preset temperature or intensity level, a measured therapeutic thermal energy, a measured thermal energy count, a preset therapeutic thermal energy, a preset therapeutic thermal energy count, a measured meridian thermal therapy time, a remaining therapeutic thermal energy, a remaining meridian thermal therapy time.

The display module is selectively connectable to one or more of the following modules: a time setting module, a temperature setting module or intensity level setting module, a therapeutic thermal measuring module, a therapeutic thermal energy setting module, and a thermal therapy time measurement module and a thermal therapy time control module.

The display module may be provided on a meridian thermotherapy instrument such as a display screen for displaying one or more of the above data, or may be provided in other devices having a display device, such as a mobile terminal.

Embodiment 5

The therapeutic thermal energy measuring system of Embodiment 1, Embodiment 2, Embodiment 3 or Embodiment 3 further comprising:

A wireless communication module for transmitting one or more of the preset time, preset temperature or intensity level, a measured therapeutic thermal energy, a measured thermal energy count, a preset therapeutic thermal energy, a preset therapeutic thermal energy count, a measured meridian thermal therapy time, a remaining therapeutic thermal energy, a remaining meridian thermal therapy time.

The wireless communication module is selectively connectable to one or more of the following modules: a time setting module, a temperature setting module or intensity level setting module, a therapeutic thermal measuring module, a therapeutic thermal energy setting module, and a thermal therapy time measurement module and a thermal therapy time control module.

The wireless communication module transmits one or more of the above data by means of wireless communication, and the wireless communication may be a wireless communication method such as Wi-Fi wireless communication or Bluetooth wireless communication, and the wireless communication technology can be achieved according to the prior art mastered by those skilled in the art. The wireless communication module can be provided in a meridian thermotherapy device or in other devices having a communication device, such as a mobile terminal. the various modules in the meridian thermal therapy device of the therapeutic heat energy measuring system can be provided in one or more different devices using the wireless communication module.

Embodiment 6

Figure 3:
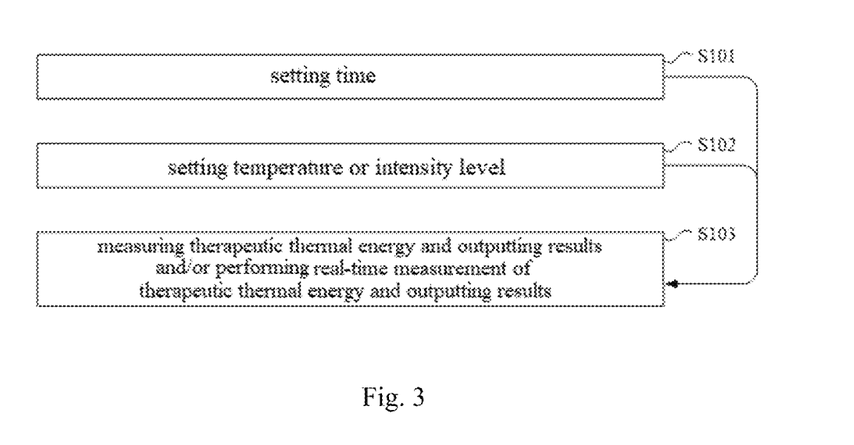
FIG. 3 shows a flow chart of the therapeutic thermal measuring method of the meridian thermal therapy device according to embodiment 1 of the present invention.

FIG. 3 shows a flow chart of the therapeutic thermal measuring method of the meridian thermal therapy device according to embodiment 1 of the present invention. The therapeutic thermal measuring method of the meridian thermal therapy device comprising the following steps:

Step S101, setting time;
Step S102, setting temperature or intensity level;
Step S103, measuring therapeutic thermal energy on the basis of a preset time and a preset temperature or intensity level by formula 1a, and outputting a result, and/or performing real-time measurement of therapeutic thermal energy on the basis of a preset temperature or intensity level and cumulative working hours of a treatment head of the meridian thermal therapy device by formula 1b, and outputting a result;

$$Q = I^2 R t_s [p_t + (T_s - T_0) \times \gamma]; \qquad \text{formula 1a:}$$

$$Q_w = I^2 R t_w [p_t + (T_s - T_0) \times \gamma]; \qquad \text{formula 1b:}$$

wherein, Q is a therapeutic thermal energy value; $Q_w$ is a therapeutic thermal energy value cumulatively generated by the treatment head of the meridian thermal therapy device; I is a current value of the meridian thermal therapy device; R is a resistance value of the meridian thermal therapy device; $T_s$ is a preset time; $t_w$ is a cumulative working time of the treatment head of the meridian thermal therapy device; $p_t$ is an initial on-off ratio of the meridian thermal therapy device; $T_s$ is a preset temperature or a temperature according to the preset intensity level; $T_0$ is a punctuation temperature of the meridian thermal therapy device or a temperature according to a punctuation intensity level; $\gamma$ is an on-off ratio change coefficient.

Counting the therapeutic thermal energy using formula 2a or 2b in Step 103:

$$F = \frac{Q}{\delta}; \qquad \text{formula 2a}$$

$$F_w = \frac{Q}{\delta}; \qquad \text{formula 2b}$$

wherein, F is a therapeutic thermal energy count value; $F_w$ is a therapeutic thermal energy count value cumulatively generated by the treatment head of the meridian thermal therapy device; $\delta$ is a conversion therapeutic thermal energy coefficient of the therapeutic thermal energy count value.

Further, the value of $\delta$ is (75-125) Cal/FU or (75-125) Cal/Kettle when the unit of measurement of the therapeutic thermal energy count value is FU or Kettle and the unit of measurement of the therapeutic thermal energy is transformed to Cal.

Embodiment 7

Figure 4:
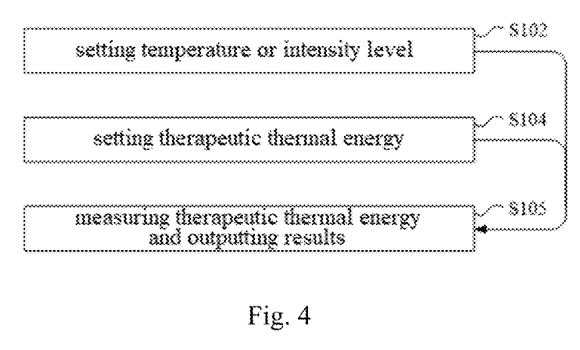
FIG. 4 shows a flow chart of the therapeutic thermal measuring method of the meridian thermal therapy device according to embodiment 2 of the present invention.

FIG. 4 shows a flow chart of the therapeutic thermal measuring method of the meridian thermal therapy device according to embodiment 6 of the present invention. The therapeutic thermal measuring method of the meridian thermal therapy device in embodiment 1 further comprising the following steps:

Step 104, setting therapeutic thermal energy;
Step 105, performing calculation of the required measuring thermal energy according to the preset therapeutic thermal energy and preset temperature or intensity level using formula 3 or 4, and outputting results;

$$t = \frac{Q_s}{I^2 R [p_t + (T_s - T_0) \times \gamma]}; \qquad \text{formula 3}$$

$$t = \frac{F_s \delta}{I^2 R [p_t + (T_s - T_0) \times \gamma]}; \qquad \text{formula 4}$$

wherein, t is a working time of the treatment head; $Q_s$ is a preset therapeutic thermal energy value; $F_s$ is a preset therapeutic thermal energy count value; $\delta$ is a conversion thermal energy coefficient of the therapeutic thermal energy count value; I is a current value of the meridian thermal therapy device; R is a resistance value of the meridian thermal therapy device; $p_t$ is an initial on-off ratio of the meridian thermal therapy device; $T_s$ is a preset temperature or a temperature according to the preset intensity level; $T_0$ is a punctuation temperature of the meridian thermal therapy device or a temperature according to a punctuation intensity level; $\gamma$ is an on-off ratio change coefficient.

Embodiment 8

The therapeutic thermal measuring method of the meridian thermal therapy device in embodiment 6 or 7 further comprising the following steps:

Step 107, storing one or more of the preset time, preset temperature or intensity level, a measured therapeutic thermal energy, a measured thermal energy count, a preset therapeutic thermal energy, a preset therapeutic thermal energy count, a measured meridian thermal therapy time, a remaining therapeutic thermal energy, a remaining meridian thermal therapy time.

Embodiment 9

The therapeutic thermal measuring method of the meridian thermal therapy device in embodiment 6, 7 or 8 further comprising the following steps:

Step 108, displaying one or more of the preset time, preset temperature or intensity level, a measured therapeutic thermal energy, a measured thermal energy count, a preset therapeutic thermal energy, a preset therapeutic thermal energy count, a measured meridian thermal therapy time, a remaining therapeutic thermal energy, a remaining meridian thermal therapy time.

Embodiment 10

The therapeutic thermal measuring method of the meridian thermal therapy device in embodiment 6, 7, 8 or 9 further comprising the following steps:

Step 109, transmitting one or more of the preset time, preset temperature or intensity level, a measured therapeutic thermal energy, a measured thermal energy count, a preset therapeutic thermal energy, a preset therapeutic thermal energy count, a measured meridian thermal therapy time, a remaining therapeutic thermal energy, a remaining meridian thermal therapy time.

A meridian thermal therapy device, the meridian thermal therapy device comprising a therapeutic heat energy measuring system which is the therapeutic heat energy measuring system of any of the above embodiments.

What is claimed is:
1. A therapeutic thermal energy measurement method of a meridian thermal therapy device, comprising a set of steps:
step S101, setting a time using a time setting module;

step S102, setting a temperature or an intensity level using a temperature setting module or an intensity setting module;

step S103, measuring a therapeutic thermal energy using a therapeutic thermal energy measurement module according to a preset time and a preset temperature or intensity level by formula 1a, and outputting a result, and/or performing a real-time measurement of the therapeutic thermal energy according to the preset temperature or intensity level and cumulative working hours of a treatment head of the meridian thermal therapy device by formula 1b, and outputting a result;

$$Q = I^2 R t_s [p_t + (T_s - T_0) \times \gamma];$$  formula 1a:

$$Q_w = I^2 R t_w [p_t + (T_s - T_0) \times \gamma];$$  formula 1b:

wherein, Q is a therapeutic thermal energy value; $Q_w$ is a therapeutic thermal energy value cumulatively generated by the treatment head of the meridian thermal therapy device; I is a current value of the meridian thermal therapy device; R is a resistance value of the meridian thermal therapy device; $T_s$ is a preset time; $t_w$ is a cumulative working time of the treatment head of the meridian thermal therapy device; $p_t$ is an initial on-off ratio of the meridian thermal therapy device; $T_s$ is a preset temperature or a temperature according to the preset intensity level; $T_0$ is a punctuation temperature of the meridian thermal therapy device or a temperature according to a punctuation intensity level; γ is an on-off ratio change coefficient.

2. The therapeutic thermal energy measurement method according to claim 1, further comprising counting the therapeutic thermal energy using formula 2a or 2b in Step 103:

$$F = \frac{Q}{\delta};$$  formula 2a $$F_w = \frac{Q}{\delta};$$  formula 2b wherein, F is a therapeutic thermal energy count value; $F_w$ is a therapeutic thermal energy count value cumulatively generated by the treatment head of the meridian thermal therapy device; δ is a conversion therapeutic thermal energy coefficient of the therapeutic thermal energy count value.

3. The therapeutic thermal energy measurement method according to claim 1, further comprising steps:

step 104, setting the therapeutic thermal energy using a therapeutic thermal energy setting module;

step 105, performing a calculation of measuring a required therapeutic thermal energy using a thermal therapy time measurement module according to the therapeutic thermal energy and preset temperature or intensity level using formula 3 or 4, and outputting results;

$$t = \frac{Q_s}{I^2 R[p_t + (T_s - T_0) \times \gamma]};$$  formula 3

$$t = \frac{F_s \delta}{I^2 R[p_t + (T_s - T_0) \times \gamma]};$$  formula 4 wherein, t is a working time of the treatment head; $Q_s$ is a preset therapeutic thermal energy value; $F_s$ is a preset therapeutic thermal energy count value; δ is a conversion thermal energy coefficient of the therapeutic thermal energy count value; I is a current value of the meridian thermal therapy device; R is a resistance value of the meridian thermal therapy device; $p_t$ is an initial on-off ratio of the meridian thermal therapy device; $T_s$ is a preset temperature or a temperature according to the preset intensity level; $T_0$ is a punctuation temperature of the meridian thermal therapy device or a temperature according to a punctuation intensity level; γ is an on-off ratio change coefficient.

4. The therapeutic thermal energy measurement method according to claim 1, further comprising a step:

step 107, storing one or more of the preset time, preset temperature or intensity level, a measured therapeutic thermal energy, a measured thermal energy count, a preset therapeutic thermal energy, a preset therapeutic thermal energy count, a measured meridian thermal therapy time, a remaining therapeutic thermal energy, and a remaining meridian thermal therapy time using a data storage module.

5. The therapeutic thermal energy measurement method according to claim 1, further comprising a step:

step 108, displaying one or more of the preset time, preset temperature or intensity level, a measured therapeutic thermal energy, a measured thermal energy count, a preset therapeutic thermal energy, a preset therapeutic thermal energy count, a measured meridian thermal therapy time, a remaining therapeutic thermal energy, and a remaining meridian thermal therapy time using a display module.

6. The therapeutic thermal energy measurement method according to claim 1, further comprising a step:

step 109, transmitting one or more of the preset time, preset temperature or intensity level, a measured therapeutic thermal energy, a measured thermal energy count, a preset therapeutic thermal energy, a preset therapeutic thermal energy count, a measured meridian thermal therapy time, a remaining therapeutic thermal energy, a remaining meridian thermal therapy time using a wireless communication module.

* * * * *